United States Patent [19]

Collins et al.

[11] Patent Number: 5,447,861
[45] Date of Patent: Sep. 5, 1995

[54] CONTINUOUS MAMMALIAN CELL LINES HAVING MONOCYTE/MACROPHAGE CHARACTERISTICS AND THEIR ESTABLISHMENT IN VITRO

[75] Inventors: Geary W. Collins, Wilmington; Michael T. Largen, Newark, both of Del.

[73] Assignee: E. I. du Pont de Nemours and Company, Wilmington, Del.

[21] Appl. No.: 878,253

[22] Filed: May 4, 1992

Related U.S. Application Data

[63] Continuation-in-part of Ser. No. 266,877, Nov. 2, 1988, abandoned.

[51] Int. Cl.⁶ ............................................... C12N 5/08
[52] U.S. Cl. .............................. 435/240.21; 435/240.2; 435/240.23
[58] Field of Search ............ 435/240.2, 240.21, 240.23

[56] References Cited

U.S. PATENT DOCUMENTS

| | | | |
|---|---|---|---|
| 4,064,007 | 12/1977 | Choay et al. | 424/115 |
| 4,135,975 | 1/1979 | Lichtman et al. | 435/240.23 |
| 4,770,781 | 9/1988 | Schmidt et al. | 530/351 |
| 5,198,356 | 3/1993 | Lieberman et al. | 435/240.2 |

FOREIGN PATENT DOCUMENTS 8804687  6/1988  WIPO ........................... C12N 5/00

OTHER PUBLICATIONS

Salhuddin et al., J. Exp. Med., 155:1842–1857(1982).
Markham et al., Biotechniques, S(5):432–443 (1987).
Wardley et al., Immunology, 39:67–73 (1990).
Journal of Immunological Methods, 99 (1987) 259–270, Emily Shacter.
Journal of Immunological Methods, 65 (1983) 319–332, Courtney R. Johnson, Dennis Kitz and J. Russell Little.
Lowenstein et al, Exp. Hernatol, 15:685–694 (1987).
Franklin et al, Immunol. Commun., 11:477–489 (1982).

*Primary Examiner*—Stephen G. Walsh
*Assistant Examiner*—David L. Fitzgerald

[57] ABSTRACT

Continuous mammalian cell lines having characteristics of immature monocytes and/or macrophages which have been established from normal mammalian cells, continuous human cell lines having characteristics of immature monocytes and/or macrophages which are substantially free of malignant cells, and a method for establishing such cell lines through long-term culturing of normal mammalian cells with periodic, partial medium changes during culturing are provided.

4 Claims, No Drawings

CONTINUOUS MAMMALIAN CELL LINES HAVING MONOCYTE/MACROPHAGE CHARACTERISTICS AND THEIR ESTABLISHMENT IN VITRO

CROSS-REFERENCE TO RELATED APPLICATIONS

This application is a continuation-in-part of application Ser. No. 07/266,877, filed Nov. 2, 1988, now abandoned.

FIELD OF THE INVENTION

This invention relates to continous cell lines having characteristics of immature monocytes and/or macrophages and to a method for establishing them in vitro from normal mammalian sources.

BACKGROUND ART

Monocytes and macrophages are derived from hematopoietic stem cells. Such stem cells are also precursors for other cells such as erythrocytes, granulocytes, platelets and lymphocytes. Once stem cells are committed to the monocyte/macrophage pathway, they differentiate into promonocytes. Promonocytes are small, round cells which exhibit extensive cell division and little to no adherence to tissue culture flasks. Promonocytes mature into monocytes which are slightly larger, exhibit less cell division and more adherence. Finally, monocytes mature into macrophages which are large cells which exhibit no cell division and strong adherence.

Continuous cell lines having monocyte/macrophage characteristics have a number of important uses. These cell lines can be used for characterization of normal monocyte/macrophage growth, maturation and function, for large-scale production of cytokines and mRNA for the production of recombinant DNA clones specifying these cytokines, for growth of viral and parasitic pathogens and, possibly, for production of vaccines for such viral and parasitic pathogens and for evaluation of drugs for such viral and parasitic pathogens.

Use of continuous cell lines having monocyte/macrophage characteristics has been limited by the difficulty in establishing such lines. Continuous cell lines have been isolated from both mouse and human sources, but the number of cell lines available for use is small, particularly those cell lines from human sources.

With few exceptions, human cell lines having monocyte/macrophage characteristics have been established only from leukemic patients. Thus, the cells of such cell lines are malignant and are less useful than cells of cell lines established from normal human cells for the study of normal human cell functions. In addition, cell lines established from malignant cells are less desirable than cell lines established from normal cells for the production of cytokines and vaccines since the malignant cells can secrete undesirable by-products which are difficult to separate from the final product. The two most commonly used human cell lines are U-937 [Sundstrom et al., Int. J. Cancer, 17:565–577 (1976)] and THP-1 [Tshuchlya et al., Int. J. Cancer, 26:171–176 (1980)]. Both cell lines were established by adapting leukemic cells to in vitro growth. Another human cell line occasionally used for production of monocyte/macrophage products is HL-60 [Collins et al., Nature, 270:347–349 (1977)]. This cell line appears to have been established from a less differentiated precursor cell since the cells, depending on which stimulating agent is used, can be stimulated to express some of the properties of a granulocyte or a monocyte/macrophage. HL-60 was also established from leukemic cells.

In the mouse system, approximately fifteen continuous cell lines having monocyte/macrophage characteristics are available. These cell lines were established from mice bearing tumors which occurred either spontaneously or, in most cases, were induced by treatment of mice with oncogenic viruses or chemical carcinogens.

The establishment of continuous cell lines having monocyte/macrophage characteristics from normal mice by the transfection of replication-defective oncogenic virus (SV40) DNA into peripheral blood monocytes has been described [Schwarzbaum et al., d. Immunol., 132:1158–1162 (1984)]. A similar technique has also been used to establish human cell lines [Nagata et al., Nature, 306:597–599 (1983)]. The human cell lines resulting from this technique are growth-factor dependent, requiring the addition of exogenous colony stimulating factor (CSF) for in vitro growth. Continuous cell lines requiring no exogenous growth factors have been established by introducing oncogenes from oncogenic viruses into monocytes [Pierce et al., 1986 Clinical Haematology (England) 15:573–596]. Cell lines containing oncogenes and viral DNA are not characteristic of normal cells and, therefore, are less desirable than cells lines established from normal cells for studying normal cell functions. In additon, these cell lines are less useful than cell lines established from normal cells for production of vaccines or cytokines because of harmful by-products which can be secreted by the oncogenes or virus particles.

Continuous cell lines having monocyte/macrophage characteristics have been established from some normal mammalian sources. Wardley et al.[Immunology, 39:67–73 (1980)]describe the establishment of continuous monocyte/macrophage cell lines from peripheral blood monocytes of a variety of species, including goat, pig, guinea-pig, sheep, rabbit, dog and cat. Very frequent, approximately daily, total medium changes were necessary to establish the cell lines. Attempts at establishing cell lines from human, horse and cattle sources were unsuccessful.

Salahuddin et al.[J. Exp. Med., 155:1842–1857 (1982)] describe the establishment of long-term (approximately five months) cell lines composed of replicating human monocytes/macrophages in suspension and adherent non-replicating macrophages. These cell lines were all established from peripheral blood of Epstein-Barr Virus (EBV)-seronegative individuals. Eventually, most of the cell lines terminated as non-replicating mature macrophages. However, two cell lines, which have grown in culture for several years, were established from peripheral blood mononuclear cells of one individual [Salahuddin et al., Biotechniques, 5(5):432–443 (1987)]. The method for preparing such cell lines required cell separation on supplemented discontinuous Percoil gradients, growth in media containing hydrocortisone and vitamin $D_3$, weekly, total medium changes, gentle, continuous agitation, and peripheral blood from EBV-seronegative individuals. The method described by Salahuddin et al. appears to have worked only in two instances of approximately twenty-eight instances tried without any apparent explanation of the successes and failures or selection criteria for the starting cells other than that they be EBV-seronegative. In the absence of a reliable method for producing such cell lines the happenstance creation of just two cell lines is not enabling to those wishing to reproduce Salahuddin et al.'s work.

There exists a need for a method for establishing continuous cell lines in vitro having monocyte/macrophage characteristics from a wide variety of normal cell sources and mammalian species.

SUMMARY OF THE INVENTION

The method of this invention for establishing continous mammalian cell lines in vitro having characteristics of immature monocytes and/or macrophages comprises the steps of:

(a) preparing a suspension of normal mammalian starting cells of monocyte and/or macrophage lineage or a precursor thereof;

(b) culturing said suspension of starting cells in a medium; provided that when the starting cells are human cells, the medium is supplemented with a serum substitute containing insulin, transferrin and a selenous acid salt;

(c) incubating said suspension of starting cells for a time sufficient to lead to the formation of adherent cells;

(d) removing non-adherent cells by changing medium;

(e) culturing the adherent cells in a medium with periodic, partial medium changes until said cells are at or near confluence on the growth surface; and (f) culturing said confluent or near confluent cells for a time sufficient to produce cells of uniform morphology which divide rapidly and which, after dilution, are capable of growing to confluence in a medium without the addition of exogenous growth factors other than insulin and transferrin.

This invention also comprises a continuous human cell line having characteristics of immature monocytes and/or macrophages which is substantially free of malignant cells and of products of malignant cells. The invention further comprises a continuous human or mouse cell line having characteristics of immature monocytes and/or macrophages which is established from normal mammalian cells. This invention is not limited to the cell lines themselves, but includes any clones, mutations, modifications, or genetic material of such cell lines.

Applicants have made the following biological deposits under the terms of the Budapest Treaty:

| Depositor Identification Reference | Int'l. Depository Designation | Date of Deposit |
| --- | --- | --- |
| Human hematopoietic cell line, MD | CRL 9850 | 10/7/88 |
| Human hematopoietic cell line, PH | CRL 9851 | 10/7/88 |
| Human hematopoietic cell line, PMC2 | CRL 9852 | 10/7/88 |
| Human hematopoietic cell line, 90196B | CRL 9853 | 10/7/88 |
| Human hematopoietic cell line, EL 1 | CRL 9854 | 10/7/88 |
| Human hematopoietic cell line, SC | CRL 9855 | 10/7/88 |
| Human hematopoietic cell line, KMA | CRL 9856 | 10/7/88 |

As used herein, "ATCC" refers to the American Type Culture Collection international depository located at 12301 Parklawn Drive, Rockville, Md. 20852 U.S.A. The "ATCC No." is the accession number to cultures on deposit with the ATCC.

DESCRIPTION OF THE INVENTION

The present invention relates to a method for establishing continuous mammalian cell lines in vitro having monocyte/macrophage characteristics from normal mammalian cells. The cells comprising the cell lines of the instant invention are believed to be precursors of monocytes/macrophages. The cells exhibit surface markers and produce cytokines characteristic of monocytes/macrophages, but exhibit cell morphologies and cell growth patterns characteristic of myelomonocytic precursors. Having been established from normal mammalian cells, the human cells comprising the cell lines of the instant invention are believed to be non-malignant and, therefore, the cell lines are believed to be free of malignant cells and of products of malignant cells while some of the mouse cell lines appear to be comprised of malignant cells. What is meant by continuous cell lines is that the cells comprising such cell lines are of uniform morphology, are rapidly dividing, and, after dilution, are capable of growing to confluence in a medium.

The present invention is not limited to cell lines established by the method described herein, but also includes any clones, mutations, modifications, and genetic material of such cell lines. By modification is meant any introduction of foreign genetic material into cells comprising the cell lines.

Starting cells from which such cell lines can be established include normal spleen, lymph node and thymus cells of mammals. By normal is meant cells which are non-malignant. In addition, mononuclear cells from peripheral blood, such as cells from the buffy coat of a centrifuged human plasma sample can also be used. It is expected that any tissue or body fluid containing cells of monocyte/macrophage lineage, including bone marrow, can be used as a source of starting cells for the instant invention.

If necessary, the starting cells can be treated to prepare a single cell suspension. For example, spleen cells can be homogenized and passed through a sieve. Peripheral blood cells exist as single cells and need not be treated.

When using human spleen as a cell source, several different methods of preparation can be used. Fresh spleen tissue can be stored for as long as one day in Iscove's medum containing 10% fetal calf serum (FCS) and subsequently homogenized. The resulting cells can be plated directly into T-25 or T-75 tissue culture flasks. Alternatively, the spleen can be homogenized, the resulting spleen cells can be fractionated by centrifugation on a Ficoll-Hypaque gradient and frozen in liquid nitrogen. These frozen cells can be thawed and used as starting cells for establishment of a continuous cell line.

The single cell suspension can be placed into a tissue culture flask and cultured in a standard tissue culture medium such as Iscove's medium containing glutamine and 2-mercaptoethanol and supplemented with 10% (v/v) FCS. It is expected that other tissue culture media can also work satisfactorily.

While animal sera other than FCS can be used in the instant invention, FCS is preferred. Different manufacturer lots of FCS can contain different growth factors and, therefore, not all lots of FCS can be used. Those lots of FCS which have been screened and found effective for growth of myeloma and hybridoma cells are also effective for growth of cells in the instant invention.

The medium used in the instant invention is preferably prepared with pyrogen-free water to prevent contamination of medium with lipopolysaccharide (LPS). LPS can stimulate cell differentiation resulting in mature, non-dividing macrophages. Water and medium which are free of lipopolysaccharide are preferred for use in carrying out the instant invention.

The medium used for establishing cell lines from human cells is standard tissue culture medium which is supplemented with a serum substitute containing insulin, transferrin, a selenous acid salt, such as sodium selenite, and possibly other growth factors, such as 1% Nutridoma-SP (Boehringer-Mannheim). Addition of such a serum substitute is important for the establishment of continuous human cell lines. Such cell lines could not be established in the absence of a serum substitute containing insulin, transferrin and a selenous acid salt.

The concentration of starting cells necessary to start culturing is dependent on the starting cell source. For example, when spleen cells are used as starting cells, a concentration of between $2.0 \times 10^5$ and $7.5 \times 10^6$ cells/20 mL of medium in a T-75 tissue culture flask can be used. When using peripheral blood cells, a higher concentration of approximately $1.0 \times 10^7$ cells/10 mL of medium in a T-25 tissue culture flask or $2.0 \times 10^7$ cells/20 mL of medium in a T-75 tissue culture flask is needed.

While the steps of the method for carrying out the instant invention can be described in complete and clear terms, the events occurring during each step are difficult to delineate. Different types of starting cells exhibit different growth patterns to lead to possible overlap between the steps as described and the events occurring during the process may overlap for each starting cell.

After plating the suspension of starting cells for culturing, the cells are left undisturbed for a time sufficient to lead to the production of adherent cells, which can take approximately two days. Adherent cells are those cells which have attached to the growth surface. Culturing of these adherent cells can lead to continuous cell lines having monocyte/macrophage characteristics.

Following this period, the tissue culture flasks are gently rocked to resuspend any non-adherent cells and the medium is removed, for example, by aspiration and replaced with approximately 10 mL of fresh medium in a T-25 flask and 20 to 25 mL of fresh medium in a T-75 flask. Non-adherent cells are those cells which have not attached to the growth surface but remain floating in the supernatant. It is important to remove these non-adherent cells as they can grow and die in the supernatant, depleting nutrients and producing toxic substances which can prevent growth of new cells.

Thereafter, periodic, preferably weekly medium changes in which approximately half of the medium is removed and replaced with an equal amount of fresh medium are performed. Since peripheral blood cells require a higher cell concentration, the removed medium is centrifuged to separate cells from spent medium. These cells can be reintroduced into the tissue culture flask with fresh medium. Partial medium replacement is believed to be a crucial step of the instant invention. It is thought that partial medium replacement allows for growth factors, which have been secreted by the cells, to accumulate in the tissue culture flask. These growth factors stimulate growth of the cells. Periodic, partial medium replacement is required until the cells are at or near confluence on the growth surface. Cells are at or near confluence when a substantially continuous cell monolayer can be observed on the growth surface. Once the cells are at or near confluence, periodic partial medium replacement is no longer necessary since the cells are at a concentration which is high enough to replenish growth factors quickly even if all medium is removed.

Once the cells are at or near confluence, there are other circumstances which can require total medium replacement. For example, when using a higher cell concentration to start culturing, rapid growth of a variety of adherent cell types can occur. Such an overgrowth of cells can deplete nutrients and space necessary for growth and attachment of new cells. Some adherent cells can be thinned and removed by gentle scraping with a cell scraper. After scraping, cell debris should be removed by replacing all the medium with fresh medium. Culturing of the remaining cells can continue with periodic partial or total medium changes.

Usually, between one to five months from plating of the cells, depending on the type of individual cell culture, rapidly dividing cells of uniform morphology can be observed in the supernatant. Moderately dividing cells can often be observed prior to the establishment of a continuous cell line, but such cells will be diverse in size and morphology.

A continuous cell line has been established when cells of uniform morphology which divide rapidly and which, after dilution, are capable of growing to confluence in a medium are produced. Cells which divide rapidly have a doubling time of 24 to 48 hours. Cells of a continuous cell line can be diluted to a low cell concentration, such as $1.0 \times 10^3$ cells/mL, and are capable of growing to confluence in medium after such a dilution.

The continuous cell line established by the method of this invention is not a homogenous cell line. However, once a continuous cell line has been established, cells can be cloned to produce a homogeneous cloned cell line. In some cases, certain cells require a larger amount of growth factor than a single cell can produce and, therefore, such cells cannot be cloned. However, such cells can be maintained as non-cloned cell lines and can subsequently be cloned after growing in vitro for a longer period.

Cell lines of the instant invention, both cloned and non-cloned, can be maintained without the addition of exogenous growth factors in serum-free medium containing insulin and transferrin. Exogenous growth factors include purified growth factors, such as hormones and recombinant proteins, as well as undefined conditioned media, such as colony stimulating factor and L-cell conditioned medium. The cell lines of the instant invention express surface antigens which indicate that they are of monocyte/macrophage lineage. For example, mouse cell lines express surface antigens such as Mac-1, Mac-2 and Mac-3 and human cell lines express surface antigens such as Mo 1 and M1. These cell lines also synthesize and secrete various cytokines, such as IL-1 and hybridoma growth factor (HGF), which are characteristic cytokines secreted by monocytes/macrophages. A cytokine is a protein molecule which regulates other types of cells. The use of the cell lines of the instant invention to produce HGF for the serum-free growth and in vitro production of monoclonal antibodies by B cell hybridomas has been described in applicants' assignee's, E. I. du Pont de Nemours & Company, copending application Ser. No. 114,054, filed Oct. 26, 1987.

The cell lines of the instant invention having monocyte/macrophage characteristics are capable of producing a variety of cytokines, including IL-1, HGF, tumor necrosis factor (TNF), and interferons. As shown in the Example below, IL-1 and HGF are produced by at least some cell lines of the instant invention. While some cell lines of the instant invention can produce IL-1 and HGF on their own, other cell lines can require stimulation with a stimulating agent, such as lipopolysaccharide, before such cell lines can produce IL-1 and HGF. The cell lines of the instant invention can be maintained in serum-free synthetic medium without the addition of exogenous growth factors other than insulin and transferrin, thus simplifying purification of secreted IL-1 and HGF. Thus, the cell lines of the instant invention can provide a homogeneous source of large quantities of specific secreted products, which are readily purified, as well as the mRNAs encoding those products.

A number of different viruses and parasites can replicate in monocytes/macrophages in general and in the cell lines of this invention having monocyte/macrophage characteristics. One such virus is Human Immunodeficiency Virus 1 (HIV-1). This virus replicates in both T lymphocytes and monocytes/macrophages. Surface antigen CD4 is at least a portion of the receptor to which the virus binds. As shown in the Example below, most of the cell lines of the instant invention are positive for the surface expression of CD4.

HIV-1 can be produced by infecting cells with virus and allowing the virus to replicate inside the cells. Infection can be accomplished by incubating the cells with supernatant from a known HIV-1-producing cell line, such as CEM 3B, for a time sufficient to allow for infection, approximately 72 hours. The infected cells can be incubated for a time sufficient to allow the virus to replicate inside the cells, approximately one week. The cells can be lysed, for example, with a detergent to release virus which can be readily isolated from the lysed cells. Currently, HIV-1 production utilizes viral infection of T lymphocyte cell lines. However, some isolates of HIV-1, particularly those isolates from the nervous system, replicate considerably better in monocytes/macrophages than in T lymphocytes. Thus, the cell lines of the instant invention can be useful for production of viruses which replicate better in monocytes/macrophages than in T lymphocytes.

Viruses and viral lysates can be used for diagnostic purposes and for therapeutic purposes, such as killed virus vaccines. The cell lines of the instant invention can be used for production of such vaccines. In addition, the cell lines of the instant invention can be used for studying regulation of viral expression in monocytes/macrophages and for in vitro evaluation of therapeutic drugs against such viruses. Both uses are important in that there is speculation that HIV may establish latent infections in monocytes/macrophages and, upon activation, cause disease. The cell lines of the instant invention can also be used in studies to determine what activates viruses within monocytes/macrophages, to evaluate drugs for their ability to inactivate viruses in their latent state inside monocytes/macrophages, and to evaluate drugs to ascertain their inability to activate viruses.

There is a number of viruses and parasites which replicate in monocytes/macrophages and are pathogenic to mammalian species other than man. It is expected that cell lines having monocyte/macrophage characteristics can be isolated from these species and can be used for production of such viruses and parasites, which, in turn, can be used for diagnostic and therapeutic purposes.

The ability to establish cell lines having monocyte/macrophage characteristics from most individuals presents an opportunity to study the genetic basis of cellular cooperation in the human immune system. Genetic histocompatibility is required for antigen presentation by monocytes/macrophages to T and B lymphocytes. Although it is possible to prepare continuous T and B lymphocyte cell lines from most individuals, it has not been possible until now to prepare cell lines having monocyte/macrophage characteristics from most individuals. Studies using cell lines of the instant invention may ultimately provide increased opportunity for therapeutic intervention in the human immune system.

The Example below illustrates the invention.

EXAMPLE

Establishment and Utilization of Continuous Cell Lines Having Monocyte/Macrophage Characteristics A. Establishment of Continuous Cell Lines from C3H/HeJ Mice One female C3H/Hej mouse was sacrificed and the spleen and one lung were removed. The spleen was passed through a #150 mesh screen into 30 mL of Iscove's Modified Dulbecco's Medium supplemented with hypoxanthine (13.6 mg/mL), thymidine (7.6 mg/mL), L-glutamine (2 mM), and 10% (v/v) fetal bovine serum. Ten mL of medium containing the spleen cells was then plated into each of three T-25 culture flasks. The lung was passed through a #150 mesh screen into 10 mL of the above supplemented medium and plated into a T-25 flask.

After a 2-day incubation period, the flasks were gently rocked to mix non-adherent cells. The medium was removed from each flask by aspiration and replaced with 5 mL of fresh medium. One week after plating of the cells, an additional 5 mL of fresh medium was added to each flask bringing the total volume in each flask to 10 mL. Seventeen days after plating, 5 mL of medium was removed from each flask and replaced with 5 mL of fresh medium. On day 23, near confluent cells were observed on tissue flask surfaces. Ten mL of medium was removed from each flask and 10 mL of fresh medium was added. On day 28, the cells in each flask were thinned by scraping a portion of each flask's inner surface with a plastic cell scraper. Ten mL of medium, including the scraped cells, was removed from each flask and 10 mL of fresh medium was added. Rapidly dividing cells of uniform morphology were observed in flasks containing spleen and lung starting cells. Approximately one month later (two months from plating of cells), these cells were cloned by limiting dilution in 96-well plates. The resulting cell lines were designated SPL HeJ.A and L HeJ.B, respectively.

B. Establishment of Continuous Cell Lines from Human Spleen PMC

Approximately fifteen 1-cm×1-cm sections of human spleen from a kidney cadaver donor were obtained immediately following death. The tissue sections were placed in the medium described in Example A and stored overnight on ice. The following day, the sections were passed through a #50 wire mesh screen and then through a #150 wire mesh screen. The cells were placed into two 50-mL sterile centrifuge tubes, each containing approximately 40 mL of medium. The tubes were centrifuged for ten minutes at approximately 400×g. The cell pellet from one tube was resuspended in 9 mL of fetal bovine serum and 1 mL dimethyl sulfoxide. The resuspended cells were divided and frozen in ten 1-mL freezing vials and stored in liquid nitrogen for further studies.

A cell suspension was prepared from the second tube by bringing the cell pellet to a volume of 20 mL with Iscove's Medium containing L-glutamine (2 mM), 2-mercaptoethanol ($5.0 \times 10^{-5}$M), 10% (v/v) fetal bovine serum, and 1% Nutridoma SP (Boehringer-Mannheim). The cell concentration was $1.5 \times 10^6$ cells/mL. T-75 flasks were numbered 1 to 9 and 10 mL of medium was added to each. Ten mL of the cell suspension was added to flask #1, yielding a total volume of 20 mL. A 1:2 dilution of the remaining cell suspension was prepared by adding 10 mL of the cell suspension to the 10 mL of medium in flask #2, mixing, removing 10 mL of the mixture, and adding the 10 mL to flask #3. Similar 1:2 dilutions were prepared through flask #9.

The next day, flasks #1 to #5 were gently rocked to resuspend erythrocytes and other non-adherent cells. The medium containing non-adherent cells in each flask was completely removed and replaced with 20 mL of fresh medium. Many adherent cells were observed in flasks #1 to #3.

Weekly, half of the medium from each flask was removed and replaced with fresh medium. Of the nine flasks, flasks #1 and #7 were lost due to yeast contamination and flasks #8 and #9 were discarded after no viable cells were observed. At day 28, rapidly dividing cells of uniform morphologer were observed in flasks #2, #5 and #6. Flask #4 did not show evidence of rapidly dividing cells until approximately three months after plating of the cells. Cells from flask #2, designated PMC-2, were cloned by limiting dilution and the clones were designated PMC-2.1, PMC-2.2 amd PMC-2.3. The continuous cell line PMC-2 was deposited in the American Type Culture Collection (ATCC), 12301 Parklawn Drive, Rockville, Md. 20852 on Oct. 7, 1988 and was given ATCC accession number CRL 9852.

C. Establishment of A Continuous Cell Line from Human Peripheral Blood

Forty mL of fresh blood was obtained from a single donor. The blood was collected into 10 mL Vacutainer tubes (Becton-Dickinson) containing sodium heparin. The tubes were centrifuged at 500×g for 20 minutes. The buffy coat was removed with a Pasteur pipette. The buffy coat cells were added to 12 mL of Iscove's medium containing L-glutamine (2 mM) and 2-mercaptoethanol ($5 \times 10^{-5}$M) but lacking serum or serum substitutes. Two mL of cells were plated into each of several flasks containing different media supplemented with various types of sera, plasma and serum substitutes. The supplements included, by volume, 10% human serum+1% Nutridoma-SP; 10% fetal bovine serum+1% Nutridoma-SP; 5% fetal bovine serum+5% human serum+1% Nutridoma-SP; 5% human plasma+5% fetal calf serum; 10% human plasma, and synthetic medium [(SM), consisting of 50% Dulbecco's Modified Eagle's Medium (DME, Hazelton-Dutchland) and 50% Hank's F-12 Medium (F-12, Hazelton-Dutchland) supplemented with 2.4 mM L-glutamine, 5 μg/mL bovine insulin (Sigma Chemicals), 30 gg/mL human transferrin (Sigma Chemicals), and 2.6 ng/mL sodium selenite]+10% human serum. The total volume of each flask was 10 mL. Two days after plating, the flasks were gently rocked to resuspend non-adherent cells. All medium containing non-adherent cells was removed and replaced with fresh medium. Weekly medium changes were performed as described in Step B above, except that the removed medium was centrifuged to collect cells from the medium and these cells were reintroduced into the flask with fresh culture medium.

One month after the initial plating of the cells, the flask containing medium supplemented with 10% fetal bovine serum+1% Nutridoma-SP contained many rapidly dividing cells of uniform morphology. The flasks containing media supplemented with 5% fetal bovine serum+5% human serum+1% Nutridoma-SP; 5% human plasma+5% fetal calf serum; and synthetic medium contained some cells. The flasks containing media supplemented with 10% human serum+1% Nutridoma-SP and 10% plasma contained very few cells.

The cells in the flask containing medium supplemented with 10% fetal bovine serum+Nutridoma-SP were cultured for approximately three months after initial plating of the cells so that the cells reached confluence in the supernatant. The resulting cell line was designated SC and was not cloned. Continuous cell line SC was deposited in the ATCC on Oct. 7, 1988 and was given ATCC accession number CRL 9855.

D. Flow Cytometry Characterization of Human Continuous Cell Lines

To determine the lineage of cell lines established by the method of the instant invention, the surface phenotype of some human cell lines established in Steps B and C was determined using well characterized murine monoclonal antibodies and analyzing fluorescence in an Epics C flow cytometer. The monoclonal antibody reagents were obtained commercially (Coulter Corp. and Becton-Dickinson) and the panel of monoclonal antibodies included those which recognize the monocyte/macrophage surface markers Mo1, Mo2, M1, M2, M3, My4, My7, and My9 as well as those which recognize surface markers for normal and leukemic B and T lymphocytes.

Both cloned and non-cloned cell lines were examined. In the following tables, cloned cell lines are indicated by a "." followed by a clone number; non-cloned cell lines have no ".". Cell lines PMC-2 and SC were established in Example 1B and 1C, respectively. Cell lines 90196B.1, MD.1, KMA.1, PH.1,and EL 1 were established from frozen spleen cells. The spleens were cut into sections as described in Step B and placed into a mechanical tissue disruptor (Stomacher) in RPMI 1640 medium supplemented with 5% (v/v) fetal calf serum. The resulting cell suspension was separated by centrifugation on a Ficoll-Hypaque gradient and the cells were stored frozen in 10% dimethyl sulfoxide and 40% fetal calf serum at a concentration of $1 \times 10^8$ cells/mL. The frozen cells were thawed and used to establish continuous cloned cell lines as described in Step B. The non-cloned continuous cell lines 90196B, MD, KMA, PH, and EL 1 were deposited in the ATCC on Oct. 7, 1988 and were given ATCC accession numbers CRL 9853, CRL 9850, CRL 9856, CRL 9851, and CRL 9854, respectively.

Cells from individual cell lines, grown in T-25 flasks in Iscove's Modified Dulbecco's Medium (IMDM)+10% fetal calf serum+1% Nutridoma-SP as described in Step C, were counted and $3 \times 10^6$ cells were washed with TIL buffer (Hank's Balanced Salts Solution supplemented with 2% fetal calf serum and 0.02% sodium azide). The cells were preabsorbed in 1% goat serum to reduce non-specific background binding and were centrifuged at 400×g. The resulting cell pellets were added to 1.5 mL of TIL buffer and 50-μL aliquots were placed into wells of a 96-well microtiter plate. The cells were incubated for 20 minutes with a first antibody specific for a surface marker. The plate was centrifuged and the cells were washed with TIL buffer. A fluorescein isothiocyanate (FITC)-labeled second antibody specific for the first antibody was added to the plate and, after a 20 minute incubation, the plate was centrifuged and the labeled cells washed with TIL buffer. Negative controls were incubated with only the second antibody. The labeled cells were fixed with paraformaldehyde in TIL buffer and were either analyzed immediately or stored at 4° C. until analysis.

The labeled cells were analyzed using an Epics C flow cytometer (Coulter Corp.) set at a small forward angle scatter parameter to analyze viable labeled cells selectively. Labeled non-viable cells present in the cell sample during the assay will exhibit large light scatter due to non-specific binding of FITC-labeled second antibody. Such light scatter interferes with the interpretation of assay results. To eliminate such interference, only viable cells which exhibit small light scatter were analyzed. As labeled cells streamed through the flow chamber, fluorescence excitation was achieved using a focused 488 nm line from an argon laser. Approximately 2,000 to 5,000 labeled cells were routinely analyzed for each sample. After subtracting the values of the negative control cells, the percentage positive cells for each surface marker was calculated. For all cells, the background staining with the second antibody reagent was 15% or less of the total cells. Table 1 summarizes the results. A percentage of cells positive of at least 20% was considered a positive for expression of a surface marker. The monocyte/macrophage cell line U-937 was included as a control.

TABLE 1

% Cells Positive for Monocyte/Macrophage Markers

| Cell Line | Mo1 | Mo2 | M1 | M2 | M3 | My4 | My7 | My9 |
|---|---|---|---|---|---|---|---|---|
| 90106B.1 | 17 | 6 | 93 | 20 | 7 | 77 | 32 | 74 |
| MD.1 | 9 | 6 | 75 | 5 | 7 | 23 | 19 | 7 |
| PMC-2 | 42 | 7 | 66 | 15 | 17 | 18 | 14 | 17 |
| SC | 55 | 5 | 99 | 2 | 10 | 97 | 85 | 84 |
| KMA.1 | 38 | 19 | 83 | 20 | 24 | 87 | 86 | 89 |
| PH.1 | 33 | 12 | 93 | 13 | 13 | 83 | 57 | 73 |
| EL 1 | 91 | 5 | 98 | 8 | 14 | 98 | 99 | 97 |
| U-937 | 87 | 0 | ND* | 1 | 58 | 96 | 96 | 96 |

*Not determined

The results listed above indicate that the cell lines of the instant invention expressed surface markers characteristic of monocyte/macrophage lineage. All cell lines were positive for M1 and, except for cell lines PMC-2 and MD.1, were positive for My4, My7 and My9.

Although the detailed data are not shown above, most cell lines were positive for surface expression of Dr (Ia) antigens and, except for cell lines PMC-2 and MD.1, expressed the receptor for complement component C3. The expression of Dr (Ia) antigens and C3 are also characteristic of cell lines of monocyte/macrophage lineage.

Some of the markers expressed were surprising. B cell markers B 1 and B4 were expressed by most of the cell lines. B2 was expressed by only the MD.1 cell line. Markers B1, B2 and B4 are characteristic of normal B cells, but are also expressed by various non-T cell leukemias as well as leukemic cells undergoing blast crisis. Cell line U-937, which is of the monocyte/macrophage lineage, also expressed the markers B1 and B4. Because of the U-937 results, it is believed that the cell lines of the instant invention, with the exception of cell lines MD.1 and PMC-2, are probably cell lines corresponding to a normal stage of cell differentiation which, although committed to the monocyte/macrophage lineage, normally express some markers of lymphoid lineage.

The cell lines of the instant invention also expressed several different surface markers characteristic of cells of the T lymphocyte lineage. The most notable of these markers were those recognized by T4, OKT4, OKT4A, and Leu3a antibodies, which all recognize epitopes of the HIV-1 receptor, CD4. Although it is known that normal monocytes/macrophages express CD4 on their surface and are susceptible to HIV-1 infection, the expression of other T cell surface markers by the cell lines of the instant invention was surprising. However, the well characterized U-937 cell line also expressed such T cell surface markers.

E. Cytochemical Characterization of Human Cell Lines

To determine the lineage of the cell lines of the current invention further, the cells were treated with a series of cytochemical stains and analyzed by light microscopy. The reagents and procedures were obtained from commercial kits (Sigma Chemical Company). The stains used were periodic acid-Schiff (PAS), myeloperoxidase, naphthol AS-D chloroacetate esterase, naphthyl Ac AC esterase, and Sudan Black B. "+" and "−" refer to positive and negative staining, respectively. "±" refers to weak staining. "D" and "G" refer to diffuse and granular staining, respectively. "ND" indicates staining was not determined for that sample. The stains used serve to differentiate cells of the monocyte/macrophage lineage from cells of other lineages.

TABLE 2

Cytochemical Characterization of Human Cell Lines

| Cell Line | Myeloperoxidase | PAS | Naphthol AS-D CA Esterase | Naphthyl Ac AC Esterase | Sudan Black B |
|---|---|---|---|---|---|
| PMC 2.3 | − | − | +/−G | − | − |
| MD.2 | − | +G | +/−G | − | − |
| KMA.1 | +/− | +D,G | +D,G | +G | + |
| 90196B.1 | + | +G | +G | +G | + |
| PH.1 | ++ | +D | +D | +G | + |
| SC | + | +G | +G | +G | + |
| EL 1.3 | + | +G,D | +G,D | +G | + |
| U-937 | + | + | +D,G | +G | + |
| THP-1 | ND | ND | ND | +G | + |

Cells from all of the cell lines of the instant invention, except for cell lines MD.2 and PMC-2.3, stained positively for all of the stains. Positive staining for all of the stains is characteristic for cells of the monocyte/macrophage lineage.

F. Secretion of Cytokines by Human Cell Lines

Representative samples of cell lines established by the method of the instant invention were stimulated with bacterial lipopolysaccharide (LPS) and phorbol myristate acetate (PMA) and assayed for production of IL-1 and Hybridoma Growth Factor (HGF).

a. IL-1 Production by Human Cell Lines

Cells were grown to approximately $5.0 \times 10^5$ cells/mL in synthetic medium and either not stimulated or stimulated with 20 ng/mL of PMA or 10 μg/mL of S. minnesota RE 595 LPS (Ribi Immunochemicals) for 48 hours. Both PMA and LPS are known to stimulate IL-1 production in cells of the monocyte/macrophage lineage. Cell-free synthetic medium was used as a control. The cells were removed by centrifugation and supernatants were sterilized by membrane filtration. IL-1 activity of the supernatant was determined by a thymocyte co-mitogenic assay as described by Gery et al.(J. Exp. Med. 136:128 1972) using co-stimulation of C3H/HeJ thymocytes by suboptimal doses of phytohemagglutinin (PHA), a T cell mitogen. Units of IL-1 activity were determined by comparison to standard recombinant IL-1.

TABLE 3

IL-1 Production by Human Cell Lines

| Cell Line | Stimulating Agent (IL-1 Activity) | | |
|---|---|---|---|
| | None | PMA | LPS |
| SC | 1.2 | 3.0 | 12.2 |
| EL 1.3 | <0.1 | <0.1 | 10.4 |
| KMA.3 | <0.1 | <0.1 | <0.1 |
| 90196B.1 | <0.1 | <0.1 | 15.1 |
| KMA.1 | <0.1 | <0.1 | <0.1 |
| EL 1.1 | <0.1 | <0.1 | <0.3 |
| PMC-2.1 | 5.3 | 3.5 | 15.9 |
| MD.1 | 9.4 | 5.4 | 22.0 |
| PH.1 | <0.1 | <0.1 | <0.1 |
| Control | <0.1 | | |

As can be seen from Table 3, most of the cell lines of the instant invention produced IL-1 either alone or with stimulation. The cell lines produced more IL-1 when stimulated with LPS than when not stimulated or when stimulated with PMA. Increased IL-1 production after stimulation with LPS is consistent for cells of the monocyte/macrophage lineage. The failure of cell lines KMA.3, KMA.1 and PH.1 to produce IL-1 emphasizes the differences of individual cell lines of the instant invention and is not an indication that these cell lines are not of the monocyte/macrophage lineage.

b. HGF Production by Human Cell Lines

Attempts to establish an assay for the presence of human HGF using human hybridoma cells as targets have been unsuccessful due to high background growth of the hybridoma cells even in the absence of exogenous HGF. Therefore, human hybridoma growth factor activity was determined using an assay with mouse hybridoma cells as targets. Mouse HGF has been shown to promote non-adapted, serum-free growth of many mouse hybridomas. Based upon interspecies stimulation of target cells by other human lymphokines and monokines, it was expected that promotion of serum-free growth of mouse hybridoma cells would be indicative of a protein(s) which would also promote the growth of human hybridoma cells.

A mouse hybridoma cell line was plated at low density in a non-protein basal tissue culture medium supplemented with a low protein content serum substitute. Samples of conditioned medium containing growth factors were added and after incubation for approximately 72 hours, proliferation and/or activation was measured as described below and compared to control cells to which no conditioned medium had been added.

For the preparation of conditioned medium, the human cell lines were first adapted to growth in low protein, synthetic medium (SM) as described in Step C. Alternatively, the cell lines were adapted to growth in Iscove's Medium supplemented with 1% Nutridoma-SP (Boehringer-Mannheim). The human cell lines were adapted to growth in SM or Iscove's+Nutridoma-SP by growing for several passages in either medium at which time the growth rate was approximately 80-90% of that obtained in medium containing 10% FBS. The cell lines were grown in serum-free medium since serum, if present in the sample to be assayed, would score positive for HGF activity. The cell lines were grown to near confluence ($7-10 \times 10^5$ cells/mL) and either nothing, LPS (E. coli 055:B5W, Difco) at a final concentration of 0.1 μg/mL or 1 μg/mL, or phorbol myristate acetate at a final concentration of 20 ng/mL was added. After incubation for 48 hours, supernatant was removed from each cell line and cells and cellular debris were removed by centrifugation at $48,000 \times g$ for 15 minutes. Additional smaller debris was removed and the solution rendered sterile by passage through sterile 0.22 micron filters. Supernatant from each cell line was frozen in aliquots at $-70°$ C. or stored for several weeks at 4°C.

For the HGF activity assay, 20 μL aliquots of supernatant from each human cell line were added to wells of 96-well plate whole area cells (Costar Scientific). Supernatants from two cell lines of monocyte/macrophage lineage, U-937 and THP-1, and cell-free medium were used as positive and negative controls, respectively. Murine hybridoma cells (line 24E/10) were added to each plate at 8000 cells/well and grown for 72 hours in a humidified $CO_2$ incubator at 37° C. The medium used was Iscove's medium supplemented with 1% Nutridoma-SP (Boehringer-Mannheim). Supernatants were removed from individual wells with an 8-channel vacuum manifold and to each well was added 100 μL of MTT [3-(4,5-dimethylthiazol-2-yl)-2,5-diphenyltetrazolium bromide] (Sigma Chemical Co., 1 mg/mL in Iscove's medium). The 96-well plates were incubated at 37° C. in a humidified $CO_2$ incubator for 3 hours. After incubation, the wells were aspirated with an 8-channel vacuum manifold. One hundred μL of isopropanol containing 0.04N HCl was added to the wells and the plates were shaken vigorously for 60 seconds to solubilize the formazan dye produced in those wells containing viable cells. The optical density of the dye solutions in the wells was measured on an automatic plate reader at 570 nm test wavelength and 690 reference wavelength. Assays were performed in triplicate and the absorbance values were averaged. The average absorbance values are shown in Table 4. Absorbance values which were 50% or greater than the negative control were considered positive.

TABLE 4

HGF Production by Human Cell Lines

| Cell Line | Stimulating Agent (Absorbance at 570 nm) | | |
|---|---|---|---|
| | None | LPS (1.0 μg/mL) | PMA (20 ng/mL) |
| SC | .133(+) | .334(−) | ND |
| KMA.1 | .131(+) | .555(+) | .508(+) |
| PMC-2.3 | .095(−) | .299(−) | .105(−) |
| 90196B.1 | .185(+) | .493(+) | .187(−) |
| EL 1.3 | .087(−) | .322(−) | .084(−) |
| PH.1 | .223(+) | .638(+) | .296(+) |
| MD.2 | .177(+) | .446(+) | .212(+) |
| U-937 | .195(+) | .846(+) | .289(+) |
| THP-1 | .127(+) | .474(+) | .129(−) |

TABLE 4-continued
HGF Production by Human Cell Lines

| Cell Line | None | Stimulating Agent (Absorbance at 570 nm) LPS (1.0 μg/mL) | PMA (20 ng/mL) |
|---|---|---|---|
| None | .069 | .273 | <.125* |

*A PMA control at the 20 ng/mL concentration was not determined. However, a PMA control at a 1 μg/mL concentration resulted in an absorbance value of .125 and it is believed the 20 ng/mL absorbance value would be less than .125.

As can be seen from Table 4, most of the cell lines of the instant invention as well as the two control cell lines, U-937 and THP-1, produced HGF either alone or when stimulated. The absorbance values for LPS stimulation at 0.1 μg/mL are not shown in Table 4 since proper controls were not determined. However, by comparing cell line absorbance values for LPS stimulation at 0.1 μg/mL with those absorbance values for LPS stimulation at 1 μg/mL, it appears that most of the cell lines did produce HGF when stimulated with 0.1 μg/mL of LPS. The failure of cell lines PMC-2.3 and EL 1.3 to produce HGF again serves to emphasize the differences of individual cell lines and is not an indication that these cell lines are not of monocyte/macrophage lineage.

G. Secretion of Lysozyme by Human Cell Lines

Secretion of lysozyme is characteristic of monocytes/macrophages. Cells from various cell lines of the instant invention were grown for 4-6 days to approximately $1 \times 10^6$ cells/mL in Iscove's Medium+10% FCS. Samples of cell-free supernatant were obtained from each cell line and assayed for lysozyme by a spectrophotometric assay utilizing freeze-dried *Micrococcus lysodecticus* cells as described by Herscowitz et al. (Manual of Macrophage Methodology, Marcel Dekker, Inc., New York, 1981, pages 240-241). Cell lines U-937 and THP-1, which are of the monocyte/macrophage lineage, were used as controls. A standard curve was prepared using hen egg white lysozyme and all concentrations of lysozyme were expressed relative to this standard curve.

TABLE 5
Secretion of Lysozyme by Human Cell Lines

| Cell Line | Lysozyme (μg/mL) |
|---|---|
| KMA.1 | <0.005 |
| MD.2 | <0.005 |
| PMC-2.1 | <0.005 |
| EL 1.3 | <0.005 |
| SC | 1.24 |
| PH.1 | 2.72 |
| 90196B.1 | 0.57 |
| U-937 | 1.39 |
| THP-1 | 0.57 |

As can be seen from Table 5, cell lines PH.1, SC and 90196B.1, as well as the two control lines, U-937 and THP-1, all secreted lysozyme. The failure of cell lines MD.2, PMC-2.1, EL 1.3 and KMA.1 to secrete lysozyme again emphasizes the differences of individual cell lines of the instant invention and is not an indication that these cell lines are not of monocyte/macrophage lineage.

H. Replication of HIV-1 in Human Cell Lines

Human cell lines PH.1, MD.1, KMA.1 and 90196B.1 were grown to a high density and $1 \times 10^8$ cells from each line were collected by centrifugation, washed and resuspended at a concentration of $5 \times 10^6$ cells/mL in supernatant of CEM 3B cells, an HIV-1-producing cell line, to infect the cell lines with HIV-1. After 72 hours, the cells were collected by centrifugation and resuspended in fresh Dulbecco's Modified Eagle's Medium at $2 \times 10^5$ cells/mL. Samples of these suspensions were collected from each cell line before HIV-1 infection and at Day 6, 10, 12, 14, 16 and 20 post-infection. Cells were removed by centrifugation and cell supernatant was saved. No visible changes in cell morphology or growth pattern were noted during the infection period.

Each cell supernatant was treated with 0.5% Triton X-100 and frozen until the Day 20 cell suspensions were collected. All cell samples were then assayed for HIV-1 p24 viral antigen using a p24 ELISA detection kit (Du Pont). Non-infected and chronically infected T cell lines CEM and H9 were included as positive and negative controls, respectively.

TABLE 6
p24 ELISA Assay for Human Cell Lines

| Cell sample | O.D. (410 nm) | | | | | |
|---|---|---|---|---|---|---|
| | PH.1 | MD.1 | KMA.1 | 90196B.1 | CEM | H9 |
| Non-infected | .050 | .042 | .051 | .060 | — | — |
| Day 6 | .380 | 1.352 | .300 | .312 | — | — |
| Day 10 | .400 | 1.415 | .328 | .271 | — | — |
| Day 12 | .212 | 2.054 | .219 | .175 | — | — |
| Day 14 | .192 | 2.325 | .202 | .183 | — | — |
| Day 16 | .172 | 2.455 | .184 | .111 | — | — |
| Day 20 | .070 | 2.682 | .170 | .101 | — | — |
| Negative control | — | — | — | — | .087 | .069 |
| Positive control | — | — | — | — | 2.682 | >3.0 |

As can be seen in Table 6, HIV-1 replicated in cell line MD.1 of the instant invention as evidenced by the production of the HIV-1 structural protein, p24. All cell lines other than MD.1 evidenced some production of p24 at Days 6 and 10, but the level of p24 decreased after that point. It is not known whether the p24 produced at Days 6 and 10 was residual p24 from the CEM 3B supernatant or whether the low level of p24 was indicative of a latent or low level productive infection. This experiment was not designed to detect HIV-1 infections not resulting in shed p24 antigen detectable by ELISA leaving open the possibility that certain cell lines of this invention accumulate intracellular virus and/or viral antigens.

We claim:

1. A method for establishing a human or murine cell line in vitro from normal cells, said cell line comprising precursor cells of monocytes and/or macrophages, wherein said precursor cells are weakly adherent relative to adherent mature cells, exhibit uniform morphology, have a doubling time of 24-48 hours, and are capable of growing to confluence in a medium after dilution to a low cell concentration, comprising the steps of:

(a) preparing a suspension of normal human or mouse cells of monocyte and/or macrophage lineage or of precursor cells thereof;

(b) culturing said suspension in a medium consisting of a standard tissue culture medium and a supplement, said supplement consisting of animal serum when murine cells are cultured or an animal serum plus a serum substitute when human cells are cultured, said serum substitute containing insulin, transferrin, and a selonous acid salt;

(c) incubating said suspension of starting cells for a time sufficient to lead to the formation of adherent cells;
(d) removing non-adherent cells by changing medium;
(e) culturing the adherent cells remaining after step (d) in a medium with periodic, partial medium changes until said cells are at or near confluence on the growth surface; and
(f) culturing said confluent or near confluent cells for a time sufficient to produce weakly adherent cells relative to adherent mature cells of uniform morphology which have a doubling time of 24–48 hours, and which, after dilution to a low cell concentration, are capable of growing to confluence in a medium without the addition of exogenous growth factors.

2. The method of claim 1 additionally comprising the cloning of the cells produced in step (f).

3. The method of claim 1 wherein the human cells are selected from the group consisting of peripheral blood cells and spleen cells.

4. A human cell line selected from a group consisting of ATCC accession number CRL 9850, CRL 9851, CRL 9852, CRL 9853, CRL 9854, CRL 9855, and CRL 9856.

* * * * *